United States Patent [19]

Garabedian

[11] Patent Number: Plant 5,987

[45] Date of Patent: May 19, 1987

[54] GRAPEVINE, GARLATE

[76] Inventor: John M. Garabedian, 3104 E. Huntington Blvd., Fresno, Calif. 93702

[21] Appl. No.: 791,426

[22] Filed: Oct. 25, 1985

[51] Int. Cl.[4] ..... A01H 5/00

[52] U.S. Cl. ..... Plt./47

[58] Field of Search ..... Plt./47

*Primary Examiner*—James R. Feyrer

*Attorney, Agent, or Firm*—Worrel & Worrel

[57] ABSTRACT

A grapevine particularly characterized by its grapes which are generally similar to those of the "Garmeria" grapevine, but characterized as to novelty by producing grapes which are ready for harvest several days after the "Garmeria" grapevine and furthermore by producing berries which have a strong attachment to the pedicel and being larger and more elongated in shape than the "Garmeria" variety.

1 Drawing Figure

BACKGROUND OF THE NEW VARIETY

The present invention relates to a new and distinct variety of grapevine to be known as the "Garlate", and more particularly to a grapevine which is closely similar in physical characteristics and fruit to the "Garmeria" grapevine (U.S. Plant Pat. No. 5,047), but from which it is distinguished in producing a berry which matures several days later than the "Garmeria", is larger in size, and which furthermore has a much stronger berry attachment than the "Garmeria".

For decades, the applicant has endeavored to produce new and distinct varieties of fruit trees and vines in an effort to upgrade the quality of his products. In his labors to produce these new and distinct varieties, the applicant has, as a regular practice, selected parent vines having desirable characteristics, cross-pollinated the subject parents, and thereafter studied the progenies produced to ascertain its quality. The instant variety "Garlate", is a product of the aforementioned procedure.

ORIGIN AND ASEXUAL REPRODUCTION OF THE NEW VARIETY

The applicant cross-pollinated two vines that were selected from a group of seedlings that were of a Lebanese variety of grapevine. This first cross-pollination and selection was made some time in 1977 at the applicant's ranch located at 5841 E. Kings Canyon Road, Fresno, Calif. Shortly thereafter, the noteworthy characteristics of the subject variety were detected and appreciated by the applicant. Thereafter, the subject variety was asexually reproduced by cuttings made from the parent seedling vine, at the applicant's designated ranch. The characteristics of the grapevines resulting from the asexual reproduction were identical to those of the original parent seedling.

BRIEF DESCRIPTION OF THE DRAWING

The accompanying drawing is a color photograph of two bunches of grapes of the subject variety, several leaves showing their dorsal and ventral coloration, and a typical section of the vine of the subject variety.

DETAILED DESCRIPTION

Referring more specifically to the pomological details of this new and distinct variety of grapevine, the following has been observed under the ecological conditions prevailing in the applicant's designated ranch near Fresno, Calif.

VINE

Size: Large.

Form: Horizontal, dense, and tender.

Growth: Vigorous.

Productivity: Productive; the average vine producing 20 to 30 large-sized clusters.

Trunk: Medium in size.

*Bark.*—Loose and shreddy in texture.

Canes: Long; variable in length, 68 inches through 138 inches, (173 through 533 cm.).

*Numbers.*—Medium.

*Thickness.*—Medium.

*Color.*—Reddish-Brown to brown.

*Form.*—Straight.

Nodes: Enlarged.

Internodes: Variable in length, medium to short, approximately 2.82 inches, (7.16 cm.).

*Numbers.*—The number of internodes per shoot is approximately 44.

Tendrils: Intermittent.

*Thickness.*—Slender.

*Length.*—Medium, bifurcated and trifurcated; smooth; abundant.

Flowers: Perfect flowers, having upright, and erect stamens.

*Date of bloom.*—May 10 through 15 at Fresno, Calif.; date of bloom is average as compared to other varieties of grapes. The date of bloom is approximately one week later than the Garmeria variety grapevine at Fresno, Calif.

LEAVES

Size: Variable, medium to large.

Shape: Roundish.

*Thickness.*—Average.

*Dorsal surface.*—Color — Dark Green.

*Dorsal surface.*—Texture — Smooth, and globular.

*Ventral surface.*—Color — Pale green; although it may appear also somewhat yellowish.

*Petiole.*—Length — approximately 8.6 cm.

*Petiole.*—Color — reddish.

*Lobes.*—Number — generally 3 distinct lobes appear. However, a few leaves may be found that have 5 lobes.

*Terminal lobe.*—Obtuse.

*Petiolar sinus.*—Deep; wide in width.

*Basal sinus.*—Shallow; narrow in width.

*Lateral sinus.*—Deep; narrow in width.

*Margin.*—Dentate.

*Teeth.*—Medium in depth; medium to narrow in width.

FRUIT

Maturity when described: Ripe for Harvesting; approximately October 10 through October 15 at Fresno, Calif.; ripening date is late as compared to other varieties.

Keeping quality: Unknown at the present time.

Shipping quality: Unknown; however, the berries display strong attachment to the clusters and do not shatter. The variety therefore displays some of the characteristics which indicates that it will have excellent storage and shipping qualities.

Clusters:

*Size.*—Large to very large; long in length; broad; tapering; regular; medium in density, but not compact.

*Weight.*—The average cluster weight varies from 20 oz. to 41 oz., (567–1163 grams).

Peduncle: Average in length.

*Thickness.*—Thick.

Pedicel: Average in length.

*Thickness.*—Thick; the subject variety displays a strong attachment between the berries and the pedicel.

*Pedicel.*—Warts — numerous.

Brush: Long in length; prominent; yellow in color, strong.

Berry:

*Size.*—Large; with a strongly adherent shell.

*Average weight.*—Variable, 3.05 to 4.12 grams per berry.

*Uniformity.*—Generally uniform in size and shape.

*Shape.*—Oblate and cylindrical.

*Color.*—Light Green; a typical white seedless grape color.

*Bloom.*—Medium.

Skin:

*Thickness.*—Medium thick, but tender.

*Adherence to pulp.*—Does not separate from the pulp.

Flesh: Greenish white; translucent.

*Texture.*—Soft and meaty; tender; medium juicy; sweet.

Quality: Noteworthy.

Seeds: None evident.

Use: Fresh market.

Although the new variety of grapevine possesses the described characteristics as a result of the growing conditions prevailing in the San Josquin Valley of central California, it is to be understood that variations of the usual magnitude in characteristics incident to growing conditions, fertilization, pruning and pest control are to be expected.

Having thus described and illustrated my new variety of grapevine, I claim:

1. A new and distinct variety of grapevine to be designated varietally as the "Garlate", substantially as illustrated and described, characterized principally as to novelty by its production of grapes which mature approximately October 10 through October 15 at Fresno, Calif., said grapes maturing several days later than the berries of the "Garmeria" grapevine, which it most nearly resembles, but from which it is distinguished by producing a cluster of berries which has a stronger attachment between the berry and the corresponding pedicel, by being ready for harvest several days later than the "Garmeria" variety, and having a larger, elongated, cylinder-shaped berry.

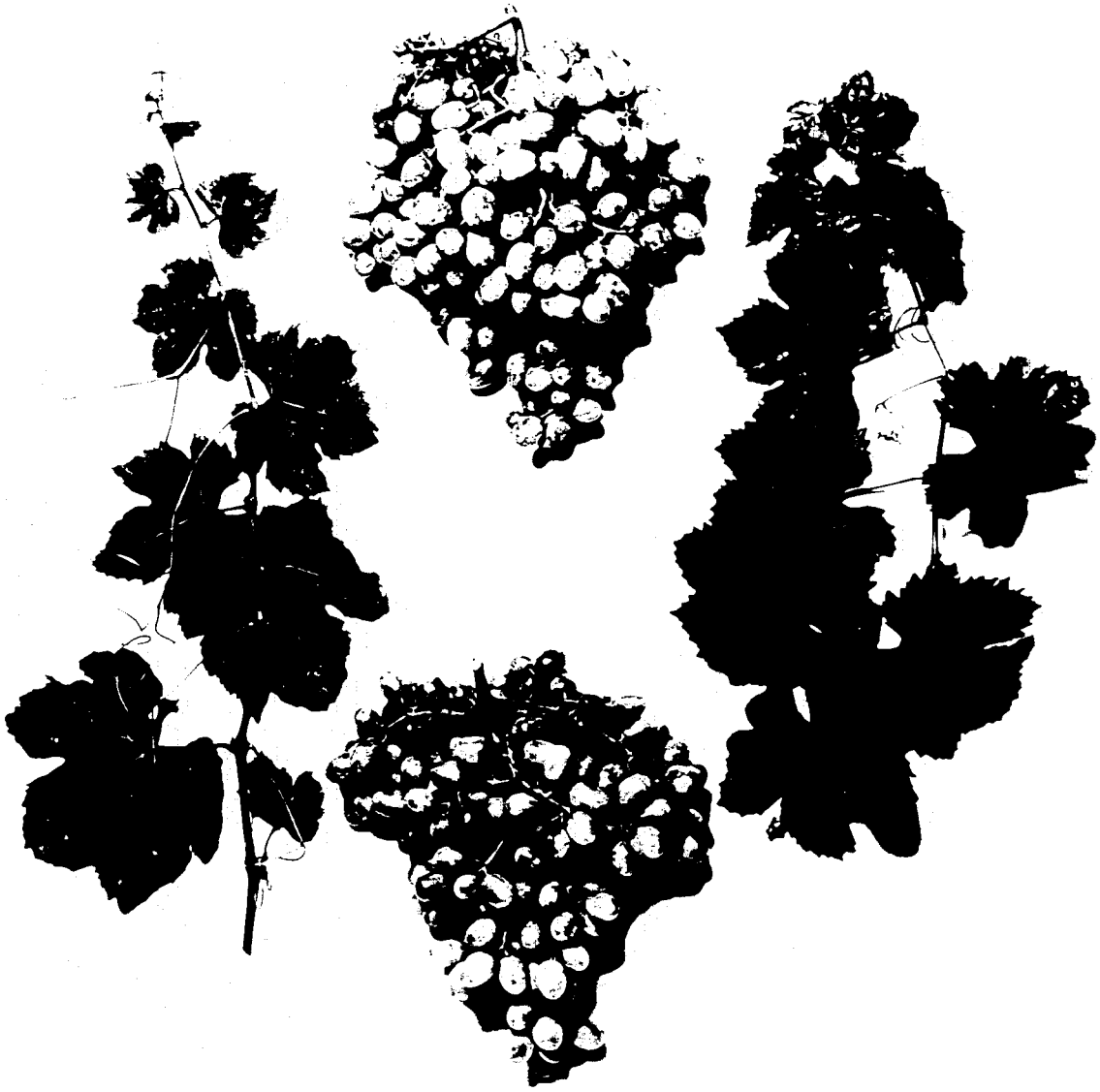

* * * * *